US012672816B2

(12) United States Patent
Fogel et al.

(10) Patent No.: US 12,672,816 B2
(45) Date of Patent: Jul. 7, 2026

(54) SYSTEMS AND METHODS FOR DETERMINATION OF COLOR VISION DEFICIENCY

(71) Applicant: Chromatech.ai, Inc., San Diego, CA (US)

(72) Inventors: Gary B. Fogel, San Diego, CA (US); Yuval Shenkal, Cardiff, CA (US); David B. Fogel, La Jolla, CA (US); Robert Penner, San Diego, CA (US)

(73) Assignee: Chromatech.AI, Inc., San Diego, CA (US)

( * ) Notice: Subject to any disclaimer, the term of this patent is extended or adjusted under 35 U.S.C. 154(b) by 0 days.

(21) Appl. No.: 19/188,573

(22) Filed: Apr. 24, 2025

(65) Prior Publication Data

US 2025/0366769 A1 Dec. 4, 2025

Related U.S. Application Data

(63) Continuation-in-part of application No. 18/784,717, filed on Jul. 25, 2024, now Pat. No. 12,285,213.

(60) Provisional application No. 63/655,905, filed on Jun. 4, 2024.

(51) Int. Cl.
*A61B 5/00* (2006.01)
*G16H 50/20* (2018.01)

(52) U.S. Cl.
CPC .......... *A61B 5/4064* (2013.01); *A61B 5/7271* (2013.01); *A61B 5/7405* (2013.01); *A61B 5/742* (2013.01); *G16H 50/20* (2018.01)

(58) Field of Classification Search
None
See application file for complete search history.

(56) References Cited

U.S. PATENT DOCUMENTS

| | | | |
|---|---|---|---|
| 4,848,898 A | 7/1989 | Massof |
| 6,424,370 B1 | 7/2002 | Courtney |
| 7,617,016 B2 | 11/2009 | Wannier et al. |
| 8,103,551 B2 | 1/2012 | Saul et al. |
| 8,249,941 B2 | 8/2012 | Saul et al. |
| 8,682,738 B2 | 3/2014 | Ivanov |

(Continued)

OTHER PUBLICATIONS

Hasrod, N., & Rubin, A. (2015). Colour vision: A review of the Cambridge Colour Test and other colour testing methods.African Vision and Eye Health, 74(1), 7 pages. doi:https://doi.org/10.4102/aveh.v74i1.23.

(Continued)

*Primary Examiner* — Collin X Beatty
(74) *Attorney, Agent, or Firm* — Lewis Kohn & Walker LLP; David M. Kohn; Kari Moyer-Henry

(57) ABSTRACT

The present invention provides novel systems and methods to determine a person's ability to perceive colors across the visual light spectrum taking into account luminance of the surrounding environment, contrast of the display being used to convey the test, or both. The present invention can be used to measure individual color vision perception at specific times or over time or in populations over time to assist with the identification of clusters of color vision deficiencies, their association with agents of both genetic and non-genetic cause and thereby improve understanding of the dynamics of color vision deficiency in individuals and across populations.

25 Claims, 3 Drawing Sheets

(56) References Cited

U.S. PATENT DOCUMENTS

| | | |
|---|---|---|
| 8,847,972 B2 | 9/2014 | Kane et al. |
| 9,070,171 B2 | 6/2015 | Guo et al. |
| 9,826,898 B1 | 11/2017 | Jin et al. |
| 9,984,658 B2 | 5/2018 | Bonnier et al. |
| 10,614,506 B2 | 4/2020 | Penner et al. |
| 10,963,944 B2 | 3/2021 | Penner et al. |
| 11,157,988 B2 | 10/2021 | Penner et al. |
| 11,389,339 B2 | 7/2022 | Schiffer |
| 11,504,625 B2 | 11/2022 | Stevens |
| 2005/0075145 A1 | 4/2005 | Dvorak et al. |
| 2008/0126962 A1 | 5/2008 | Cook |
| 2008/0294528 A1 | 11/2008 | Denk, Jr. et al. |
| 2010/0191770 A1 | 7/2010 | Cho et al. |
| 2011/0082764 A1 | 4/2011 | Flusser et al. |
| 2012/0171989 A1 | 7/2012 | Matsuo et al. |
| 2015/0116227 A1 | 4/2015 | Lin et al. |
| 2015/0123982 A1 | 5/2015 | Schoening |
| 2015/0186965 A1 | 7/2015 | Paul |
| 2016/0026253 A1 | 1/2016 | Bradski et al. |
| 2016/0026926 A1 | 1/2016 | Yeung |
| 2016/0161259 A1 | 6/2016 | Harrison et al. |
| 2017/0011452 A1 | 1/2017 | Beckham |
| 2017/0076011 A1 | 3/2017 | Gannon |
| 2017/0277365 A1 | 9/2017 | Gaidar et al. |
| 2017/0365011 A1 | 12/2017 | McIlroy et al. |
| 2019/0246895 A1 | 8/2019 | Kodimer |
| 2021/0004589 A1 | 1/2021 | Turkelson et al. |
| 2021/0133160 A1 | 5/2021 | Craft |
| 2022/0365373 A1* | 11/2022 | Ábrahám ........... G02B 27/0012 |

OTHER PUBLICATIONS

Kim S., Banashewski T., and Tannock R. (2014) Color vision in attention-deficit/hyperactivity disorder: A pilot visual evoked potential study. J. Optom. 8(2):116-130: doi: 10.1016/j.optom.2014.10.002.

Angchekar et al., An Overview Study of Various Re-Coloring and Wavelength Adjustmen Algorithm for Color Vision Deficient Individuals. IEEE International Conference on Power, Control, Signals and Instrumentation Engineering (ICPCSI-2017) (Year: 2017).

* cited by examiner

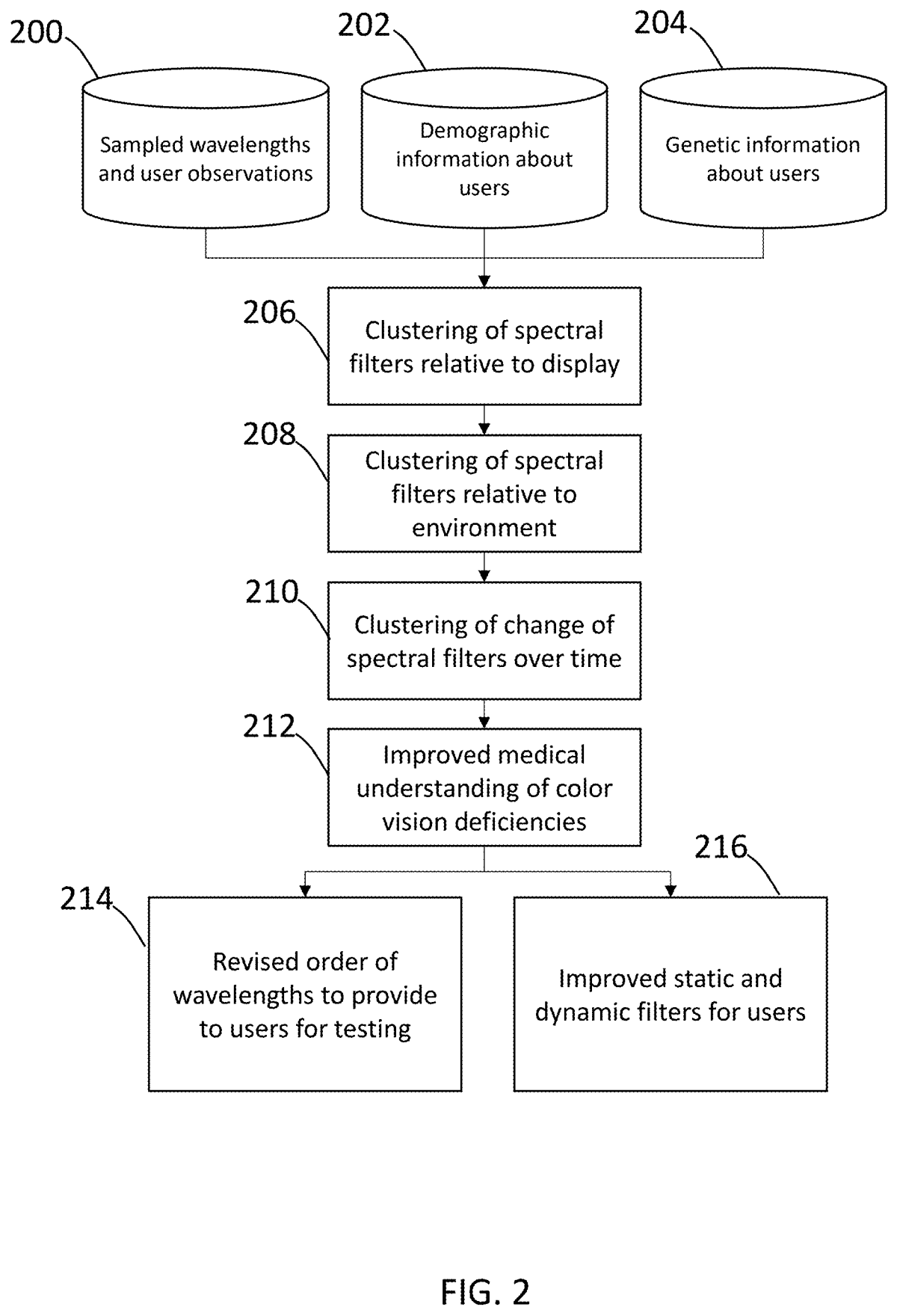

200

202

204

Sampled wavelengths
and user observations

Demographic
information about
users

Genetic information
about users

206

Clustering of spectral
filters relative to display

208

Clustering of spectral
filters relative to
environment

210

Clustering of change of
spectral filters over time

212

Improved medical
understanding of color
vision deficiencies

214

Revised order of
wavelengths to provide
to users for testing

216

Improved static and
dynamic filters for users

FIG. 2

SYSTEMS AND METHODS FOR DETERMINATION OF COLOR VISION DEFICIENCY

RELATED APPLICATIONS

This application is a continuation-in-part of U.S. application Ser. No. 18/784,717, filed Jul. 25, 2024, which claims the benefit of priority from U.S. Provisional Application No. 63/655,905 filed on Jun. 4, 2024, the contents of which are hereby incorporated by reference herein.

FIELD OF THE INVENTION

The present invention provides novel systems and methods to determine a person's ability to perceive colors across the visual light spectrum taking into account luminance of the surrounding environment, contrast of the display being used to convey the test, or both. While there are many tests for color vision, these approaches generally focus on the main types of color vision deficiencies associated with genetic determinants such as protanopia, deuteranopia, tritanopia, and achromatopsia or the rare case of tetrachromacy. Further, these tests are specific for categorizing individuals as either "normal" or into one of the pre-described known color vision deficiency types. The approaches generally lack a larger appreciation of the subtleties associated with color vision deficiencies, the large variation of possible color vision deficiencies and how these deficiencies might change with time or have association with non-genetic causes, and how these deficiencies might be corrected for individuals on a routine basis through individualized filters over a wide range of displays. The present invention can be used to measure individual color vision perception at specific times or over time or in populations over time to assist with the identification of clusters of color vision deficiencies, their variations, their association with agents of both genetic and non-genetic cause and thereby improve understanding of the dynamics of color vision deficiency in individuals and across populations.

BACKGROUND OF THE INVENTION

A wide variety of color vision tests are available to measure the color vision of a subject relative to a color standard. Such tests are used to assist mainly with the diagnosis of genetics-associated color vision deficiencies which affect 8% of males and 0.5% of females. Given normal human vision is trichromatic and results from having three types of cones cells on the retina, three main genetic color deficiencies exist such as protanopia (red-green color blindness) in which the L-cone is absent, deuteranopia (a severe form of red-green color blindness) in which the M-cone is absent, and tritanopia (blue-yellow color blindness) in which the S-cone is absent. While protanopia and deuteranopia are sex-linked, tritanopia is not and thus affects males and females at similar proportions. There are also cases of achromatopsia (a loss of all three cone cells leading to monochromacy) and there are believed to be cases of tetrachromacy (rare conditions where humans have more than three cone cells and are able to see additional colors than normal). There are even cases of chromesthesia, a special type of synesthesia that converts sounds into colors or grapheme-color synesthesia in which letters of the alphabet or numbers are associated with colors, sometimes in specific ways.

Given many professions make use of colors in different ways, screening for color vision deficiencies can be common practice in certain settings. Additionally, while specific types of color vision deficiencies have genetic causes, other changes to color vision can occur due to changes in eye health (due to exposure to lasers or ultraviolet light, degenerative eye diseases such as cataracts or macular degeneration, or diabetes), brain health (through trauma to the occipital lobe), vitamin deficiencies, medications (such as ethambutol, sildenafil, or hydroxychloroquine), or chemicals such as styrene, or organic solvents. Thus, it is critical to not only test for color vision deficiency early in life but to monitor color vision deficiency on a regular basis relative to exposure, age, and health.

The most basic tests for color vision deficiency make use of pseudoisochromatic plates to screen for specific types of color vision deficiencies such as deuteranopia, protanopia, and tritanopia. Such plates are inexpensive and fast and use a difference in the color of specific dots relative to a figure (typically a number) to help categorize subjects into these known color vision deficiencies.

The Ishihara test is a well-known set of pseudoisochromatic plates that is useful in diagnosing basic deficiencies such as red-green color deficiency or when used with subjects who cannot read but can trace differences in the images presented with their fingers. Hardy, Rand, and Ritter (HHR) plates are used to detect specific types of color vision deficiencies such as blue-yellow color deficiency. This type of pseudoisochromatic test uses shapes instead of numbers.

Color arrangement tests provide a spectrum of colors to a subject, such as a rainbow of colors, with the subject arranging these from a random distribution into an array to minimize the difference between adjacent colors. This array is then used to calculate a score from the "correct" rainbow pattern of the visible light spectrum where lower error scores are associated with more normal color vision. Several types of color arrangement tests exist including the Farnsworth-M unsell 100 hue test which provides 88 colors to the subject. This test can be used to assign subjects to specific types of known color vision deficiencies and can also be used to categorize subjects by their overall color vision as "low," "average," or "superior" based on the error score. The Farnsworth D-15 hue test reduces the number of colors to 15 and therefore saves time in the assay but does not have the specificity of the Farnsworth-M unsell 100 test.

Lantern tests project small colored lights in front of a subject and the subject is then asked to identify the color of the light being projected. Lantern tests typically make use of very particular wavelengths from the color spectrum, typically associated with occupational requirements such as those found in the U.S. Armed Forces or the U.S. Federal Aviation Administration. Such tests can identify only very specific types of color vision deficiencies but are low cost and rapid. U.S. Pat. No. 4,848,898 describes an apparatus for the projection of different colors from a combination of red, yellow, and green lights of various intensity for the purpose of ascertaining types of color vision deficiencies. This approach is analog rather than digital and is meant to have the intensity and types of lights that are illuminated correspond to the determination of the three main specific types of color vision deficiency (protanopia, deuteranopia, tritanopia).

Anomaloscopes are precise and expensive instruments used mainly in academic settings to diagnose the type and severity of color vision deficiency. One such test provides a mixture color to a subject to detect red-green color blindness. The subject is allowed to then dial the mixture color to match a reference or "test" color. Subjects are also allowed to adjust luminosity until the colors appear to match. Such tests require the subject to dynamically adjust two variables (mixture color and luminosity) and once established the deviation of those variables relative to the same variables for a color normal subject are used to assign a color vision deficiency type and the severity of that color vision deficiency. While capable of generating quantitative measures the cost and difficulty operating anomaloscopes makes them inappropriate for regular use by subjects, and therefore also makes it difficult to monitor changes in color vision deficiency over time on a subject-by-subject basis. Anomaloscopes typically make use of four different types of matches; A Rayleigh Match (test color at 589 nm (yellow), mixture color at 545 nm (yellow-green) and 670 nm (red)) to characterize red-green deficiencies in subjects, the Engelking-Trendelenburg Match (test color at 490 nm (cyan), mixture color at 470 nm (blue) and 517 nm (green)) to characterize blue-yellow deficiencies in subjects, the Pickford-Lakowski Match (test color from a tungsten bulb and mixture color at 470 nm (blue) and 585 nm (yellow-orange)) to characterize blue-yellow deficiencies in subjects, and a Moreland Match (with mixture of 480 nm (cyan-blue) and its complementary color 580 nm (yellow) and no test color) to evaluate blue-yellow deficiencies in subjects.

With the advent of computing, such color vision deficiency tests have been replicated in digital form. Such tools have many advantages as they can reduce cost, randomize the ways in which colors are presented to subjects very easily, can be made to adapt dynamically in real time to the answers provided by a subject so as to bias additional questions in specific ways and improve resulting diagnosis, and are devoid of misinterpretation by human ophthalmologists who are required to interpret qualitative tests mentioned above. However, such digital tools also have deficiencies in that the digital version of a test must be able to be validated on a wide variety of computing displays used and must be well-calibrated for use on those displays before determination of color vision deficiencies can be considered accurate. Validated digital color vision deficiency tests include the Cambridge Color Test (CCT) offered by Cambridge University in 1997, the Colour Assessment and Diagnosis (CAD) Test offered by the City University of London in 2002, and the Colour Vision Assessment provided by the University of Minho in 2016.

The CCT (Hasrod and Rubin, 2015) is a digital form of pseudoisochromatic plates where the subject indicates the presence of successive stimuli using a hand-held input device. The method uses discrimination thresholds based on these inputs to categorize protanopia, deuteranopia, or tritanopia using ellipses that show a loss of sensitivity relative to background chromaticity.

The CAD makes use of a movie displaying a moving, colored square that is itself embedded in a flickering luminance contrast noise. As this square moves and changes color, subjects with color vision deficiencies may not be able to see the colored square well and temporary (or longer term) disappearance of the square can be used as an indicator of color vision deficiency. This test is a result of Barbur et al. (1994). The digital version runs on a default factory setting of balance for most color displays and the test is to be ideally presented to a subject in a dark room to avoid issues of ambient illumination.

The Colour Vision Assessment test offered by the University of Minho (Linhares et al., 2016) is designed specifically to identify subjects with protanopia, deuteranopia, tritanopia from subjects considered color normal. The method makes use of dynamic luminance contrast noise masking (LCNM) and presents a color to a subject as circles with variable size and static random luminance. In a dynamic sense the method also includes a 10 Hz square luminance signal to each circle. Making use of 20 color hues relative to background, the method can help determine specific types of known color vision deficiencies.

For humans with normal color vision each of the three cones in the retina can detect roughly 100 different gradations of color. The total number of colors discernible by the average human is therefore 100×100×100, about 1 to 2.3 million different colors (Jacobs, G. H., 2009). Subjects with a genetic issue with one of these three cones therefore can distinguish only about 10,000 colors (Neitz et al., 2001). Despite these amazing amounts of discernable colors, most tests for color vision deficiencies focus on a select set of specific wavelengths of the light spectrum or combinations of just two wavelengths in order to classify subjects as having a specific known type of color vision deficiency. Some, like the Farnsworth tests, assay on as many as 100 colors but even this is quite limiting relative to the 10,000 to 1 million discernable colors. Additionally, these tests are pre-defined to be useful only in classifying known types of vision deficiencies. Given other types of color vision deficiencies caused by non-genetic issues are known to exist, these assays may miss entirely on for instance someone whose color vision perception has changed due to a specific medication. The universe of possible causes for changes in color vision remains largely unexplored because the methods used to assay color vision deficiency are limiting in the way they utilize the color spectrum. For example, only recently has it been hypothesized that individuals with attention-deficit/hyperactive disorder (ADHD) have difficulty with color perception of blue-yellow but not red-green stimuli due to a decreased amount of retinal dopamine (Tannock et al., 2006). A central purpose of our systems and methods is to provide a means that can discover all known and even yet uncharacterized groups of humans suffering from color vision deficiencies such that these can then be studied in a more mechanistic way.

Color vision deficiencies are not always related to genetic predisposition. It is known for instance that color vision can change in light of ocular pathologies such as cataracts or macular degeneration, or the use of specific drugs at various concentration, or pathologies associated with the brain. These types of non-genetic factors may also change with time. The subject that has a cataract develop slowly over time will have a slow change in color vision deficiency. Upon removal of the cataract the subject can have a return to some near normal or normal color vision. Measurement of the change in deviation in color vision deficiency from "normal" is therefore just as important as the measurement of the deviation at any given time, and these deficiencies do not all have to correspond to the three main known genetic predispositions that cause color vision deficiency. Further those subjects who already do have a known genetic predisposition might also have their color vision change even further if they were to have an ocular pathology such as a cataract or take a specific color vision altering medication. Thus, the space of possible color vision deficiencies is far larger than the main deficiencies recognized commonly. A new approach is needed to identify, classify, and then cluster subjects to these extra deficiencies, both statically and dynamically. Based on this information standard methods of daltonization can be applied to adjust displays in analog and digital systems. This may also include adjustment of the types of color filtering glasses that are best for each individual subject or a specific color filter or combination of color filter and brightness that is optimal for each individual subject at a given time. The identification of specific clusters of color vision deficiencies and their dynamics may also be indicative of medical issues, such as the development of cataracts, such that the systems and methods could be used for diagnosis or prognosis.

In the area of digital color vision deficiency measurements, U.S. Pat. No. 11,504,625 by Stevens describes systems and methods to determine a subject's type of color vision deficiency through a digital game where objects categorized to one of the three known visual deficiency types (protanopia, deuteranopia, and tritanopia) are provided as part of a standard dichromatic visual deficiency type set either as static or dynamic offerings within the game. Once the subject is determined to have one of the three known visual deficiencies, the gaming environment is adjusted through daltonization to improve game accessibility. This approach requires the pre-specification of vision deficiency types and corrects for them through specific static adjustments. The method cannot be used to identify novel types of color vision deficiencies, nor can it be used to dynamically adjust to changing color vision deficiency due to age or environment or luminosity. Further the method is not calibrated to the device being used by the subject to play the game and as such the color cues may be provided incorrectly to the user.

U.S. Pat. No. 9,984,658 by Bonnier et al. offers a method to determine a color transformation with an associated daltonization strength for the three main types of color vision deficiencies. The approach focuses on improved daltonization methods that transform images not using a uniform daltonization strength across the entire image but on a regional basis within the image that is being transformed to create a more realistic color transform. While insightful, this process does not assist in the determination of novel color vision deficiencies but is predicated on knowledge of the main types of color vision deficiencies and their transformation. Related U.S. Pat. No. 9,826,898 by Can et al. does include a color vision assessment as a sequence of test images displayed for a predetermined period of time with a colored patch on a neutral background or through a series of colored patches on different background colors to determine the type and severity of the main color vision deficiencies. This test does include an initial pattern of tiles with different luminance values for calibration. However, the test only supplies colors on top of other background colors, and only tests for protanopia, deuteranopia, and tritanopia. This is also an insightful means to measure and determine the type and severity of color vision deficiency, similar to digital pseudoisochromatic plates or the offering of the CCT above. This method, however, is specifically not designed to identify novel color vision deficiencies, nor measure their change with time. It is specifically meant as a method to adjust and provide displays that improve perception for those requiring enhanced accessibility.

U.S. Pat. No. 8,847,972 by Kane and Kurtz focuses on the adaptation of colors in low luminosity environments to enhance the colors as much as possible. While this approach makes use of a measurement of the external luminosity and adapts color filters it does so for the display of images through a projector and does not do so with color vision deficiencies in mind.

SUMMARY OF THE INVENTION

This invention provides systems and methods to determine a user's ability to perceive color vision across the visual light spectrum considering luminance of the surrounding environment, contrast of display being used, or both, to convey the test for the purpose of categorizing color vision. This can be used to categorize users by their type of color vision deficiencies regardless of the cause for these deficiencies whether such causes are genetic, non-genetic, or a combination of genetic and non-genetic. During the test, the visible light spectrum is sampled in an optimal manner to minimize the number of colors required to establish a color vision spectral filter. This spectral filter and its similarity to the spectral filters of other users, can be used to generate clusters of color vision deficiencies in rapid time. Once a user's color or spectral filter has been determined, methods of daltonization or inversion can be used to correct for these color vision issues using digital or analog devices or both digital and analog devices. Additionally, sounds, tones, scales, pitches, chords, or other musical forms can be associated with specific wavelengths that are observed incorrectly or not at all or collection of wavelengths observed incorrectly or not at all, helping individuals learn to "see" colors through an audio representation. Additionally the spectral filter can be used to correct images or videos by adjusting the colors or color palette used to maximize the information to the individual user, even representing wavelengths observed incorrectly or not at all through other forms on the image such as dashed lines or hash marks or other conspicuous signals to the user that the portion of the image actually represents a color that is different than they observe. The systems and methods are sufficiently easy and low cost that the tests are easy to repeat over time and can be used to monitor the health of all individuals or any vision system, even those that are based in hardware in terms of the dynamics of their color vision. Similarly, the test can be provided in different luminosities to generate sets of filters that are appropriate in different lighting conditions and thus can be used to display the right colors to the right user at the right time to maximize the proper exchange of color information from device to subject.

In one aspect, the present invention provides an opportunity to collect novel information about the nature of color vision deficiency without pre-specifying broad categories of types based on preconceived notions of color deficiencies for users with genetic conditions.

In another aspect, the present invention can be used to monitor health in a dynamic way with repeated eye tests to serve as a prognosis or diagnosis of concerning health issue.

In another aspect, the present invention can be used to pre-screen individuals for specific applications or to provide them with filters that would improve their level of performance whether for work or recreation.

In another aspect, the present invention can be used to design analog glasses that are unique to each individual based on their unique color filter.

In another aspect, the present invention can be combined with sounds, tones, scales, pitches, chords, or other musical forms to provide a combination of visual and auditory senses to help a user expand their understanding of the world.

In another aspect, the specific wavelengths of color deficiencies identified through the color test can be represented back to the user with additional marking such as lines, dashes, or squiggles as visual aids to infer that the color that observed in an image by a user with color deficiency actually represents a different color in reality.

In another aspect, knowledge of color vision deficiencies can be used by individuals to tailor chromatherapies despite not being able to see the entire visual light spectrum as the individual is already aware of what wavelengths of light they may not be able to see yet still benefit from their use for health purposes.

In another aspect the test can be applied to any device or machine making use of hardware to collect light such as those used in CCD or CMOS chips associated with electronic cameras to determine if the hardware is performing as intended.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 2 depicts a block diagram of the systems and methods to use information across many users, develop a broader understanding of the relationships between display and environment leading to a better understanding of human color perception, a spectrum of color vision deficiencies, which wavelengths are most important during testing for color vision deficiencies and sets of static and dynamic filters useful to assist in correcting for color vision deficiencies.

REFERENCE NUMERALS IN DRAWINGS

Figure 1:
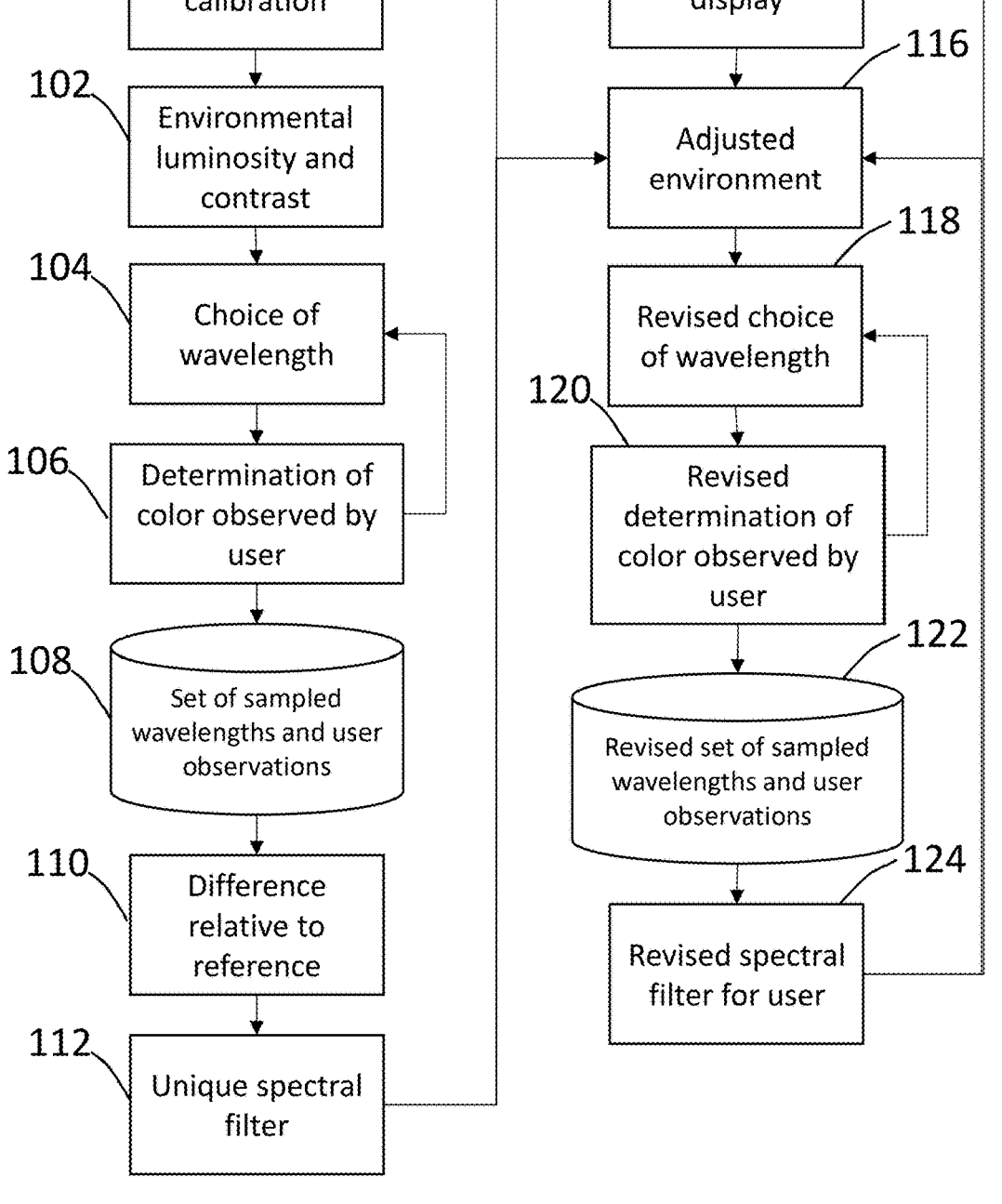
FIG. 1 depicts a block diagram of the systems and methods to determine a person's color vision deficiency across the visual light spectrum taking into account luminance of the surrounding environment, contrast of display being used to convey the test, or both.

Reference Numerals in FIG. 1

100 Display calibration
102 Environmental luminosity and contrast
104 Choice of wavelength
106 Determination of color observed by user
108 Set of sampled wavelengths and user observations
110 Difference relative to reference
112 Unique spectral filter
114 Adjusted display
116 Adjusted environment
118 Revised choice of wavelength
120 Revised determination of color observed by user
122 Revised set of sampled wavelengths and user observations
124 Revised spectral filter for user

Reference Numerals in FIG. 2

200 Sampled wavelengths and user observations
202 Demographic information about users
204 Genetic information about users
206 Clustering of spectral features relative to display
208 Clustering of spectral features relative to environment
210 Clustering of change of spectral features in time
212 Improved medical understanding of color vision deficiencies
214 Revised order of wavelengths to provide to users for testing
216 Improved static and dynamic filters for users

Figure 3:
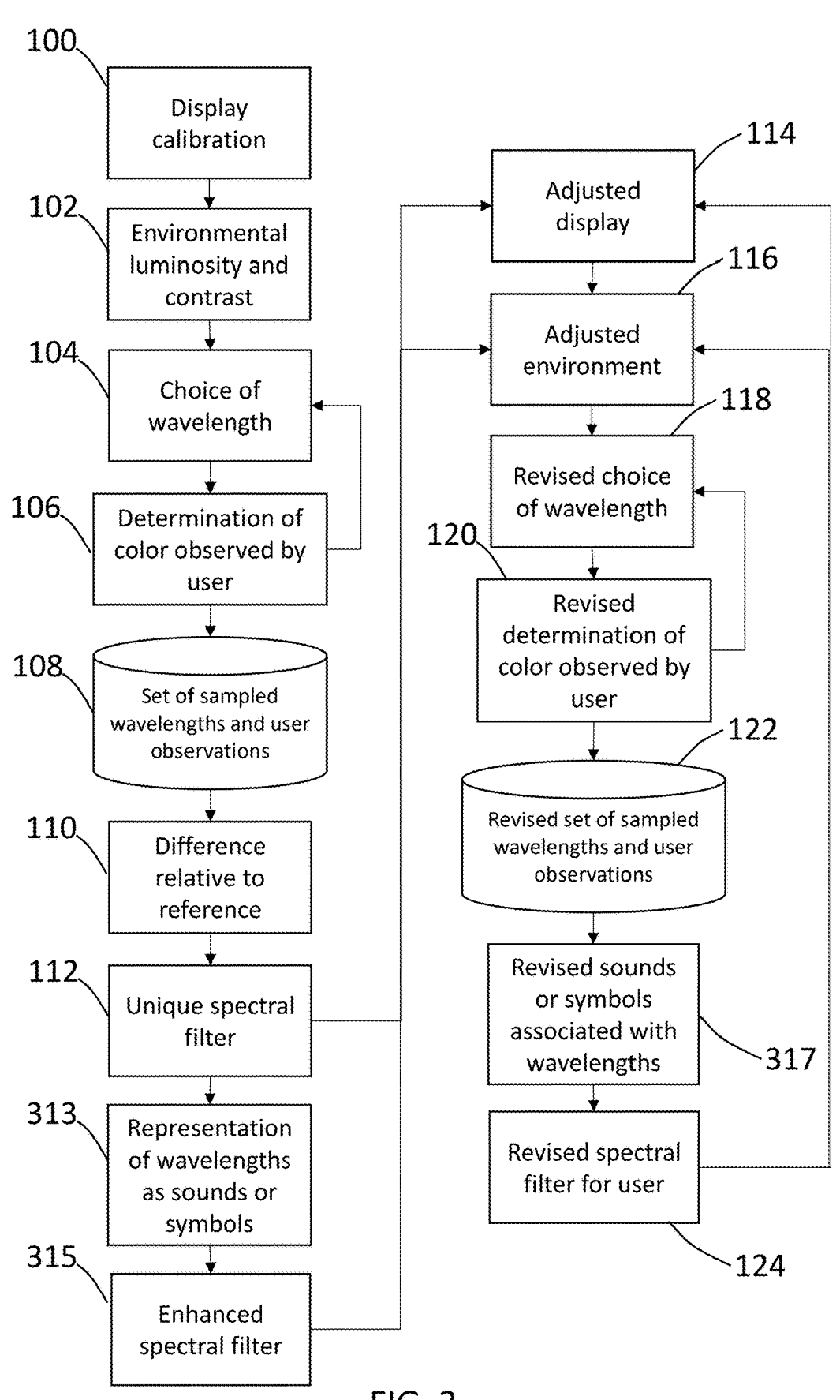
FIG. 3 depicts an alternative embodiment to the block diagram described in FIG. 1.

Reference Numerals in FIG. 3

313 Representation of wavelengths as sounds or symbols
315 Enhanced spectral filter
317 Revised sounds or symbols associated with wavelengths

DETAILED DESCRIPTION OF THE INVENTION

A preferred embodiment of the present invention is illustrated in FIG. 1. Given a user will be presented a series of colors representing various wavelengths of the visible light spectrum through a display, display calibration 100 is required for colors representing "normal" vision across the visible spectrum from 380 nm to 700 nm to ensure that the display can accurately represent all colors to a user. The environmental luminosity and contrast 102 for the user taking the test is measured and that information is also provided to the device providing the display. The luminosity and contrast or luminosity and contrast of the display is adjusted in light of the luminosity of the environment surrounding the user in order to provide colors to a user in a reasonable manner such that all wavelengths of light from 380 nm to 700 nm can be observed by the user. A cross this spectrum an initial choice of wavelength 104 to be shown to a user is selected. This selection can be made at random or with information about pre-existing color vision deficiency of the user, or about the population of users as a whole, or with the display or luminosity of the display or luminosity of the environment or some or all of these factors combined. Upon seeing the wavelength that is displayed, the user determines what color is observed 106 either as a word such as "blue" or with increased granularity such as "cyan" or "aquamarine." The wavelength that was provided to the user is then associated with the new color provided by the user and its known actual wavelength. This process of displaying a known wavelength and asking the user to determine a new associated wavelength is repeated until such time as a set of sampled wavelengths and user observations has been collected 108. The difference between the expected reference spectrum and the user's observed spectrum is calculated 110. This difference represents a spectral filter that is unique to the user and is stored 112. Wavelengths observed incorrectly can be represented as sounds or symbols 114 in an enhanced spectral filter 116 back to the user to improve interpretability even further. The colors of the display being used for the user are then adjusted 114 using a process of daltonization or other similar means to maximize the percentage of the visible light spectrum from 380 nm to 700 nm that is likely to be viewed as different colors by the user. Similarly, the luminosity of the environment can be adjusted 116 when possible in specific ways to maximize the percentage of the visible light spectrum from 380 nm to 700 nm that is viewed as different colors by the user. Once again, a process of optimization is repeated wherein the user is provided a revised choice of wavelength 118 to evaluate. This results in a revised determination of the color observed by the user 120. This process is once again repeated over many colors until a revised set of sampled wavelengths and user observations is collected 122. Revised sounds or symbols associated with wavelengths 128 can then be generated. The result of this iterative process is a revised spectral filter for the user 130 that can once again be used to adjust the display or environment to maximize the ability of the user to interpret as many unique colors as possible across the visible light spectrum.

The sampling of wavelengths to define a spectra filter above can be a tedious task for a user. Testing can be embedded within the context of an analog or digital game where specific colors are presented to the user and determination of if they can observe the color or not is made either through a direct question and answer process or via the user's real-time play in the game. In this context, the user may or may not know they are even being examined for a color vision deficiency yet playing the game with appropriately sampled colors at appropriate times allows for a determination of their spectral filter. Games also afford the opportunity to investigate and characterize color vision in young populations, even where lengthy sets of colors presented to a user may be impractical. Such games in turn can help identify color vision deficiencies of various types at very young ages, to help those afflicted with the issues recognize their difference and for educational settings to adjust educational materials accordingly.

The adjustment of displays above can be made through any number of various daltonization methods specific for the type of display that is being adjusted. In one extreme, these methods are used to adjust the display in real-time relative to changes in luminosity and contrast. For example, in the cockpit of a fighter aircraft making combat maneuvers, a digital display on the instrument panel can be adjusted dynamically to provide the right colors at the right time to the right pilot despite rapidly changing contrast and luminosity in the cockpit relative to the position of the sun. In the other extreme, a static spectral filter is provided to the maker of eyeglasses to produce a set of glasses that, on average across most expected luminosities and contrasts will improve the color vision of the user. Such spectral filters could be applied dynamically to digital glasses that are equipped with displays that allow for dynamic adjustment. Such glasses can also be equipped with eye-tracking software to discover where a user is looking at a screen or image and in the case the color of that location on a screen or image represents a portion of the visual spectrum not observed correctly, a sound can be played to the user indicating the color at that location. With eye-tracking and a means to communicate between the glasses and a computer providing an image on a screen, in light of a known user and their spectral filter from the color test, it is possible to also adjust the image on the screen dynamically to change contrast, color palette, or mark misinterpreted colors with hashes, dashes, lines, squiggles or other symbols to indicate to the user that the color really is representative of a different color in the normal visual light spectrum. For instance, in the case where the user has protanopia, it is easy to confuse darker red with black. These darker red components on an image could be marked with hash marks, indicating that portion of an image is actually dark red and not black.

Color tests can also be provided around specific use cases such as combinations of medications, the colors of those medications, and the ability of an elderly person with normal color vision but long-term issues with cataracts to be able to properly distinguish drugs by their colors. Color tests can also be associated with various types of chromatherapy to elicit specific emotional responses from perceived colors or color combinations, or to understand in advance which aspects of chromatherapy will be more or less effective due to the user's known spectral filter. However, in the context of chromatherapy, a user with a given color vision deficiency may not be able to see the color they desire to receive for health purposes or may be receiving a color that they cannot perceive accurately and for which they have no desire to receive for health purposes. Thus for any given spectral filter it is possible to associate sounds, tones, musical notes or scales that indicate if an unviewable color is actually present in the environment so that the user may take appropriate action. During the development of spectral filters, low, medium. and high tones could be used to represent three areas of deficiency. In this manner, synesthesia is used to the advantage of the participant by combining both a visual and audial understanding of colors specifically in ways that maximize information flow to the user. Users can then make use of glasses outfitted with cameras to view their world. In cases where known colors exist but are not viewable naturally by the user, the appropriate sound, tone, musical note or scale is played indicating to the user that the color (or colors) exist in the environment being viewed. Such methods can be made even more specific by associating eye-tracking software to determine where the individual is looking and associate sounds, tones, musical notes or scales with specific areas of the viewing experience.

Color tests can also be used in the food industry to distinguish types of fruit based on their colors or the ripeness of a specific type of fruit by a user. In this context, a user with some variance in color vision may not be able to properly distinguish a green unripe banana from a yellow ripe banana. Given knowledge of that user's spectral filter, the spectral filter can be used to convert still or video images and provide additional information in the form of sounds or symbols to help the user interpret ripeness properly. This could be done through the help of glasses outfitted with cameras as in the example above or via the camera in a smartphone. In the food production industry such tools can be used for quality assurance purposes in a similar manner as many of such processes rely on humans or cameras to make determinations of ripeness or quality and color vision tests such as ours can be used to enhance those tools to improve overall quality of the decisions being made based on colors.

In gaming contexts, knowledge of the user's spectral filter can be used to change colors in the game in a dynamic way based on the user's style of play. If a user is acting in a more aggressive manner, the colors of the game are adjusted towards red or "hot" colors but those that can be viewed by the user given knowledge of their spectral filter. Such color dynamics can even be used by players against other players with prior sharing of their spectral filters and access to each other's displays in the game. In these situations, one player could change the color of another player's screen as an indicator of shared hostility toward a third player, or one player could change the color of another player in a way that is maximally calming at a time when that opponent is maximally aggressive. A player could adjust colors dynamically to be a confusing or tiring to all other opponents in the game to maximize their own success. The history of colors used by players in various game contexts becomes its own unique data source that can be used to understand the benefits and deficiencies of human-color interaction once the spectral filter of each person playing the game is properly understood through the above color test. And, in light of knowledge of a user's spectral filter, one could upload that filter to a game and adjust settings, screens, skins, and other color opportunities in games to be optimized to each individual playing the game.

The set of all sampled wavelengths and user observations 200 coupled with the set of demographic information about users 202 coupled with genetic information about users 204 if known provides a unique opportunity to examine color vision deficiencies in new ways. The clustering of spectral filters relative to display 206 that was used to examine each user can inform about users and can inform about displays. It may be for instance that users with completely normal vision could not observe specific wavelengths simply because of the display being used on a portable communications device and this knowledge would be of interest to the maker of such device. It may be for instance that users with specific color vision deficiencies will have similar but not precisely identical spectral filters because of the display that was used for the test. The clustering of spectral filters relative to environment 208 that was used to examine each user can inform about users and can inform about the luminosity of different environments and the ability of those users to see colors across the visible spectrum in those different luminosities. This information can be used to help understand relationships of luminosity and changes in color and help establish operating requirements for users who are required to see specific colors in work related settings. Similarly, users with specific color vision deficiencies are likely to have similar but not precisely identical spectral filters because of the environmental luminosity that was used during the test. As users age or have other medical conditions not related to genetic predispositions for color vision deficiency their color vision may change. Repeated testing using our approach allows for the opportunity to determine a user's change in color vision over time, and to cluster the changes of special filters across multiple users over time 210. This information includes knowledge of known genetic predispositions for color vision deficiency but also the interplay of age, medicines, other neurological or ocular medical condition, or other factors that may result in color vision deficiency. Such information may be diagnostic of cause or prognostic in nature, leading to improved medical understanding of color vision deficiencies as a whole 212. In addition to improved diagnostics and prognostics such information can be used to revise the order of wavelengths to provide to users for testing 214 that are associated with specific clusters or types of medical conditions. Such information can also be used to improve static and dynamic filters for users 216 to help maximize the portion of the visible light spectrum from 380 nm to 750 nm that is considered as different colors despite genetic predispositions or other medical issues. In the case where specific sounds, tones, musical notes or scales are being used to represent colors that the user is unable to visualize correctly, as a part of the dynamics associated with the filters includes changes of the sounds over time. Such audio changes further inform the user that their color vision deficiencies are changing with time and this could also be used for prognostic or diagnostic purposes.

An alternative embodiment to the preferred methods and systems of the present invention is shown at FIG. 3. Given a user will be presented a series of colors representing various wavelengths of the visible light spectrum through a display, display calibration 100 is required for colors representing "normal" vision across the visible spectrum from 380 nm to 750 nm to ensure that the display can accurately represent all colors to a user in this alternative arrangement. Wavelengths observed incorrectly can be represented as sounds or symbols 313 in an enhanced spectral filter 315 back to the user to improve interpretability even further.

The colors of the display being used for the user are then adjusted, in accordance with adjusted display 114, using the process of daltonization or other similar means to maximize the percentage of the visible light spectrum from 380 nm to 750 nm that is likely to be viewed as different colors by the user. Revised sounds or symbols associated with wavelengths 317 can then be generated.

It is to be expected that the description of the preferred embodiment is not a limitation on variations or extensions of the invention. For example, the choice of wavelength provided to the user could be selected one at a time or selected as a set for the specific interest in identifying a specific type of color vision deficiency. Given the time required for a user to observe a wavelength and determine its color, methods of machine learning can be used to minimize the number of wavelengths to search while maximizing information across the entire visible light spectrum. For instance, an evolutionary algorithm can be used to establish successful populations of wavelengths to test with the objective of minimizing the number of total wavelengths assayed while maximizing the understanding of the user's estimated spectral filter across the entire visual light spectrum. In another embodiment, as the user determines the colors observed for a series of wavelengths provided, a clustering approach such as topological data analysis (TDA) or t-distributed stochastic neighbor embedding (t-SNE) or k-means is used to cluster users into groups of similar color vision deficiencies. A machine learning approach can then be used to assign users to clusters in a continuous fashion as observations are being made such that when the assignment exceeds a specific threshold, questioning is stopped and a diagnosis of color vision deficiency provided.

Once special filters have been optimized on an individual user basis, those same filters can be used to either update common displays for information gather such as through personal communication devices or computer or television monitors. The filters can also be used to develop personalized eyewear for the individual user such that color vision is maximized rather than relying on filters that are based solely on knowledge of genetic predispositions. Such eyewear could also include cameras or eye tracking methods as indicated previously to improve the association of visual deficiencies with sounds representing those deficiencies to users. Such filters can also be applied in digital settings to improve the quality of game play for digital gaming contexts such that the user playing the game maximizes their ability to see as many colors as possible in the game. Such filters can also be used to properly establish brightness and color filter settings unique to each user for their viewing enjoyment across all digital or analog displays.

The systems and methods can be used as an entrance test for specific work-related settings or to adjust the colors of those work-related settings to match the user that will be working in those settings. For example, as someone completes medical school, they can be evaluated through our approach to determine the color filter that is best for them. If their chosen profession is radiology, they may be expected to review digital images on a regular basis with specific colors representing benign tissue from tumor. The individual can continue to perform well as a radiologist if the colors representing those medical differences are changed in light of the known spectral filter for the user. This will improve the quality of diagnosis. The systems and methods can be used to assist children by providing them with a color test at an early age to help identify types of color vision deficiencies and provide a baseline for their individual color filter. Such color vision deficiencies may be indicative of additional medical diagnoses. For instance, given a decrease in retinal dopamine, individuals with ADHD are known to have poor blue-yellow vision (Tannock et al. 2006). This condition can be corrected through the use of methylphenidate to increase retinal dopamine and restore blue-yellow vision (Kim et al., 2014). The systems and methods can be used to uncover a large suite of color vision deficiencies and medical indications at a young age, while also being used to identify color vision deficiencies to assist with education.

The systems and methods can be used as a test to ensure that hardware systems making use of light sensing chip sets are working properly. For instance, complementary metal oxide semiconductor (CMOS) and charge coupled device (CCD) sensors are used commonly as image sensors in a variety of settings from digital cameras to mobile phones to robotics. CM OS and CCD make use of photodiodes or active pixel sensors to visualize colors. These hardware tools may have a degradation in their performance over time. Some common problems include dead pixels, hot pixels, or damage related to heat or radiation that can effect the colors that are then perceived by the hardware. Manufacturing defects can also lead to color issues. These problems manifest themselves in several ways, including "crosstalk" where a photon of light falling on one pixel in the sensor is falsely sensed by adjacent pixels leading to color-signal mixing or issues with the Bayer filter array which can lead to inaccurate color reproduction. Imperfect or incorrect color filter arrays used by the manufacturer will also lead to color assignment problems. As with human eyes, color charts to spectral response curves can be provided to identify these concerns, but our system and method minimizes the time required for such determination. Additionally, while it is possible to evaluate a hardware chip with a human-in-the-loop, comparing the output of the CM OS or CCD sensor to a normal visual spectrum, that comparison requires first evaluating the human-in-the-loop to determine that they perceive the visual spectrum properly to begin with. In the case of semi-autonomous or autonomous robotics, it is also possible to have the robot itself take the color test, determine its own spectral filter, and even apply that spectral filter rapidly as a self-corrective method.

The systems and methods can also be used to ensure that patients on medications can see the colors of pills appropriately, improving their adherence to medicines. These same approaches can be used by decision makers such as the US Food and Drug Administration to ensure that the colors used on approved drugs are visible to the largest population possible, with indication in labeling that colors of specific medicines may be difficult for people of specific color vision deficiencies to see.

The systems and methods described can also be used to help present the appropriate colors in an individualized manner to assist with chromatherapy where colors or a combination of colors and music or other sensory cues are provided to induce changes in emotional state of a human. Such colors cannot be provided appropriately unless a color filter is determined in advance for each user and chromatherapy is enhanced in the case where sounds are represented for colors interpreted by the user incorrectly and eyeglasses are used to identify those colors and play sounds, tones, musical notes, or scales when they exist in the local environment to appropriately inform the user.

It will be appreciated that details of the foregoing embodiments, given for purposes of illustration, are not to be construed as limiting the scope of this invention. Although several embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

REFERENCES

Hasrod, N., & Rubin, A. (2015). Colour vision: A review of the Cambridge Colour Test and other colour testing methods. *African Vision and Eye Health,* 74 (1), 7 pages. doi: https://doi.org/10.4102/aveh.v7411.23

Barbur, J. L., Harlow, J. & Plant, G. T. (1994) Insights into the different exploits of colour in the visual cortex. *Proc. Roy. Soc. B. Biol. Sci.* 258 (1353), doi: https://doi.org/10.1098/rspb.1994.0181

Linhares J M, João C A, Silva E D, de Almeida V M, Santos J L, Álvaro L, Nascimento S M. Assessing the effects of dynamic luminance contrast noise masking on a color discrimination task. (2016) *J Opt Soc Am A Opt Image Sci Vis.* 33 (3): A 178-83. doi: 10.1364/JOSAA.33.00A 178. PMID: 26974922.

Jacobs, G. H. (2009). Evolution of colour vision in mammals." *Philosophical Transactions of the Royal Society B.* 364 (1531): 2957-67. doi: 10.1098/rstb.2009.0039. PMC 2781854. PMID 19720656

Neitz, J., Carroll, J. & Neitz, M. Color Vision: Almost Reason for Having Eyes" *Optics & Photonics News* January 2001 1047-6938/01/01/0026/8-Optical Society of America.

Tannock, R, Banaschewski, T, and Gold D. (2006) *Behav. Brain Func.* Color naming deficits and attention-deficit/hyperactivity disorder: A retinal dopaminergic hypothesis. 2:4.

Stevens, K. E. Color blindness diagnostic system. U.S. Pat. No. 11,505,625.

Bonnier N. P., Wu J., Can J., Raymann, R. J. E. M. Displays with improved color accessibility. U.S. Pat. No. 998,465.

Can J., Bonnier N. P., Raymann, R. J. E. M, Wu J. Color vision assessment for displays. U.S. Pat. No. 9,826,898.

Kane P. J., Kurtz A. F. Adapting display color for low luminance conditions. U.S. Pat. No. 8,847,972.

Kim S., Banashewski T., and Tannock R. (2014) Color vision in attention-deficit/hyperactivity disorder: A pilot visual evoked potential study. *J. Optom.* 8 (2): 116-130: doi: 10.1016/j.optom.2014.10.002

We claim:

1. A system for the improved determination of color vision deficiencies, the system comprising: providing wavelengths of visible light from within the visible light spectrum through a display to at least one user and data storage system for storing information about the at least one user and colors they observe, wherein the at least one user is clustered relative to a manner their color observation, further wherein unique filters are developed from the difference in expected versus observed color, for the purpose of adjusting displays or environment or displays and environment to maximize the portion of the visible light spectrum that are observed by the at least one user improving their sensing of content provided through the display, wherein the portions of the visible light spectrum that are not observed properly by the at least one user are represented through other means to the at least one user, wherein such filters are used for the display.

2. A method for an improved determination of color vision deficiencies utilizing the system of claim 1, the method comprising: providing content of visible light within the visible light spectrum to at least one user through a display, wherein the content is provided in a specific order of wavelengths, wherein data is captured about an ability of the at least one user to observe the wavelengths or what colors they do observe for the wavelengths, wherein statistical approaches are used to infer a spectral filter for the at least one user based on the wavelength observations, wherein cluster analysis is used to place the at least one user on a spectrum of color vision deficiency or identify types of color vision deficiencies, wherein information across the at least one user is utilized to determine new types of color vision deficiencies, wherein the at least one user is monitored repeatedly for changes in their color vision deficiency and a spectral filter is provided back to the at least one user to assist with optimization of displays to improve their visual sensing.

3. The method of claim 2, wherein the cluster analysis of the spectral filter is one selected from the group consisting of: distance measures, k-means, topological data analysis, t-distributed stochastic neighbor embedding, and any other similar method of clustering.

4. The method of claim 2, wherein the spectral filter is combined with a process of daltonization to adjust displays for the at least one user.

5. The method of claim 2, wherein the spectral filter is used to adjust environmental luminosity of an environment surrounding the at least one user to maximize sensing of colors on the display.

6. The method of claim 2, wherein the spectral filter is used to generate eyeglasses that are optimized for the at least one user to maximize their ability to see colors.

7. The method of claim 2, wherein a specific order of wavelengths is optimized using a method selected from the group consisting of: machine learning, evolutionary computation, fuzzy logic, neural networks, deep learning, and artificial intelligence, wherein the method minimizes the time required to complete the optimization of displays while still conveying information about the at least one user and their color vision deficiencies.

8. The method of claim 2, wherein the content from the visible light spectrum and determination of colors observed by the at least one user is based in a context of a game such that a color assessment is made with or without the at least one user's knowledge.

9. The method of claim 8, wherein the game includes both colors and chromatherapy.

10. The method of claim 8, wherein the game comprises an opportunity for the at least one user to share information about their spectral filters, adjust each other's displays, and alter the game play in static or dynamic fashion for each other.

11. The method of claim 2, wherein monitoring of color vision deficiencies is made dynamically with associated updates to displays in a dynamic fashion.

12. The method of claim 2, wherein the determination of new types of color vision deficiencies is used as a diagnostic of human health or a prognostic for disease, or an associated tool for clinical trials to evaluate retinal effects of medications.

13. The method of claim 2, wherein the determination of new types of color vision deficiencies is related to non-genetic causes.

14. The method of claim 2, wherein the determination of new types of color vision deficiencies is used to fundamentally transform an understanding of the spectrum of color vision deficiencies from a simple set of three genetic causes to a larger set of non-genetic causes to the interaction of environmental factors with those genetic or non-genetic causes realizing a spectrum of color vision deficiencies, their dynamics, and a means to monitor their dynamics in users and across populations.

15. The method of claim 2, wherein the spectral filter is used to determine the colors not easily perceived by the at least one user such that chromatherapy is adjusted appropriately.

16. The method of claim 2, wherein cameras for eye-tracking are used to inform where the at least one user is looking at the display or image or video to help determine colors at specific locations and provide alternative information to the at least one user in a form of sound or symbols or altered colors or combinations of sounds or symbols or altered colors to improve understanding.

17. The system of claim 1, wherein light sensing hardware devices such as CMOS or CCD chips are evaluated for their ability to sense colors properly.

18. The system of claim 1, wherein the display can be analog, digital or a combination of analog and digital.

19. The system of claim 1, wherein the wavelengths from the visible light spectrum are provided in an ordering to minimize the time required to assign the at least one user to a known vision deficiency or classify them as having an unknown vision deficiency, or to determine them as having normal vision.

20. The system of claim 1, wherein adjustment of the display includes changes in luminosity or contrast or both luminosity and contrast.

21. The system of claim 1, wherein adjustment of the environment includes changes in luminosity.

22. The system of claim 1, wherein the wavelengths and the data storage system about the at least one user is represented in a spectral filter that is the difference of an observed wavelength relative to an expected wavelength.

23. The system of claim 1, wherein visible wavelengths that are not observed appropriately are represented to the at least one user as sounds or other visual aids.

24. The system of claim 17, wherein the light sensing hardware devices are evaluated autonomously by a robot rather than a human.

25. The system of claim 1, wherein commercial products are evaluated for quality based on color to an individual user in light of a spectral filter.

* * * * *